US00RE40572E

(19) United States
(12) Reissued Patent
Nagano et al.

(10) Patent Number: US RE40,572 E
(45) Date of Reissued Patent: Nov. 11, 2008

(54) FLUORESCENT PROBE FOR THE QUANTITATION OF ZINC

(75) Inventors: Tetsuo Nagano, 1-28-15, Amanuma, Suginami-ku, Tokyo 167-0032 (JP); Kazuya Kikuchi, Mino (JP); Tomoya Hirano, Tokyo (JP)

(73) Assignees: Sekisui Medical Co., Ltd., Tokyo (JP); Tetsuo Nagano, Tokyo (JP)

(21) Appl. No.: 11/808,125

(22) PCT Filed: Feb. 28, 2001

(86) PCT No.: PCT/JP01/01503

§ 371 (c)(1),
(2), (4) Date: Feb. 10, 2003

(87) PCT Pub. No.: WO01/62755

PCT Pub. Date: Aug. 30, 2001

Related U.S. Patent Documents

Reissue of:
(64) Patent No.: 6,903,226
Issued: Jul. 7, 2005
Appl. No.: 10/203,658
Filed: Feb. 10, 2003

(30) Foreign Application Priority Data

Feb. 28, 2000 (JP) ..... 2000-50869

(51) Int. Cl.
*C07D 311/78* (2006.01)

(52) U.S. Cl. ..... 549/391
(58) Field of Classification Search ..... None
See application file for complete search history.

(56) References Cited

U.S. PATENT DOCUMENTS

| | | | |
|---|---|---|---|
| 5,208,148 | A | 5/1993 | Haugland et al. |
| 5,874,590 | A | 2/1999 | Nagano et al. |
| 6,013,802 | A | 1/2000 | Hoyland et al. |
| 6,201,134 | B1 | 3/2001 | Nagano et al. |
| 6,441,197 | B1 | 8/2002 | Nagano et al. |
| 6,469,051 | B2 | 10/2002 | Nagano et al. |
| 6,525,088 | B1 | 2/2003 | Nagano et al. |
| 6,569,892 | B2 | 5/2003 | Nagano et al. |
| 6,833,386 | B2 | 12/2004 | Nagano et al. |
| 7,087,766 | B2 | 8/2006 | Nagano et al. |
| 2003/0157727 | A1 | 8/2003 | Nagano et al. |

FOREIGN PATENT DOCUMENTS

JP 2000-239272 9/2000

OTHER PUBLICATIONS

T. Hirano et al., "Highly Zinc–Selective Fluorescent Sensor Molecules Suitable for Biological Applications", J. Am. Chem. Soc., vol. 122, No. 49, pp. 12399–12400 (2000).

G. Walkup et al., "A New Cell–Permeable Fluorescent Probe for $Zn^{2+}$", J. Am. Chem. Soc., vol. 122, pp. 5644–5645 (2000).

J.G. Reyes et al., "A Fluorescence Method to Determine Picomole Amounts of ZN (II) in Biological Systems", Biol. Res., vol. 27, pp. 49–56 (1994).

M. Tsuda et al., "Expression of Zinc Transporter Gene, ZnT–1, is Induced after Transient Forebrain Ischemia in the Gerbil", Neurosci., vol. 17, No. 17, pp. 6678–6684 (1994).

T. Koike et al., "A Novel Biomimetic Zinc (II)—Fluorophore, Dansylamidoethyl—Pendant Macrocyclic Tetraamine 1,4,7,10–Tetraazacyclododecane (Cyclen)", J. Am. Chem. Soc., vol. 118, pp. 12696–12703, 1996.

Saibou Kougaku (Cell Technology), 17, pp. 584–595, 1998.

Tanpakushitsu Kakusan Kouso (Protein, Nucleic Acid and Enzyme), extra No., 42, pp. 171–176, 1997.

Tetsuji Kametani, Nankodo Co., Ltd., p. 215, 1997.

R. Hauglang, Handbook of Fluorescent Probes and Research Chemicals, 6th Edition pp. 503 and 531–540.

T.W. Greene, Protective Groups in Organic Synthesis, John Wiley & Sons, Inc. pp. v–xxi and 369–405.

H. Kojima et al., "Fluorescent Indicators for Imaging Nitric Oxide Production", Angew. Chem., Int. Ed. vol. 38, No. 21, pp. 3209–3212 (1999).

H. Kojima et al., "Detection and Imaging of Nitric Oxide with Novel Fluorescent Indicators: Diaminofluoresceins", Anal. Chem. vol. 70, No. 13, pp. 2446–2453 (1998).

J. Wagner et al., "Synthesis of Five Enantiomerically Pure Haptens Designed for In Vitro Evolution of Antibodies with Peptidase Activity", Bioorganic & Medicinal Chemistry, vol. 4, No. 6, pp. 901–916 (1996).

(Continued)

*Primary Examiner*—Taofiq A Solola
(74) *Attorney, Agent, or Firm*—Greenblum & Bernstein, P.L.C.

(57) ABSTRACT

A compound represented by general formula (IA) or a salt thereof useful as a fluorescent probe for zinc: wherein $R^1$ and $R^2$ represent a hydrogen atom or a group represented by formula (A), wherein $X^1$, $X^2$, $X^3$, and $X^4$ represent a hydrogen atom, an alkyl group, a 2-pyridylmethyl group, or a protective group for an amino group, and m and n represent 0 or 1 provided that $R^1$ and $R^2$ do not simultaneously represent hydrogen atoms; $R^3$ and $R^4$ represent a hydrogen atom or a halogen atom; and $R^5$ and $R^6$ represent a hydrogen atom, an alkylcarbonyl group, or an alkylcarbonyloxymethyl group, and $R^7$ represents a hydrogen atom or an alkyl group.

(IA)

(A)

9 Claims, 7 Drawing Sheets

OTHER PUBLICATIONS

Bioorg. Khim., vol. 21, No. 10, pp. 795–801 (1995).

S. Zhu et al., "Study of Bulk Morphology of Polymer Latex Films using Laser Confocal Fluorescence Microscopy" Sci. China, Ser. B: Chem vol. 41, No. 5, pp. 549–555 (1998).

H. Godwin et al., "A Fluorescent Zinc–Probe Based on Metal–Induced Folding", J. Am. Chem. Soc., vol. 118, pp. 6514–6515 (1996).

English language abstract of JP 2000–239272.

U.S. Appl. No. 10/204,417, filed Aug. 28, 2002 (National Stage of PCT/JP01/01504 filed Feb. 28, 2001) having the title "Agent for Measurement of Reactive Oxygen" (Applicants: Tetsuo Nagano et al.).

U.S. Appl. No. 10/204,418, filed Aug. 28, 2002 (National Stage of PCT/JP01/01502 filed Feb. 28, 2001) having the title "Method for Measurement by Using Longlived Excitation Fluorescence" (Applicants: Tetsuo Nagano et al.).

FLUORESCENT PROBE FOR THE QUANTITATION OF ZINC

Matter enclosed in heavy brackets [ ] appears in the original patent but forms no part of this reissue specification; matter printed in italics indicates the additions made by reissue.

This application is a 371 of PCT/JP01/01503 filed Feb. 28, 2001.

TECHNICAL FIELD

The present invention relates to a fluorescent probe for zinc that emits fluorescence by specifically trapping a zinc ion.

BACKGROUND ART

Zinc is an essential metallic element that is present in the human body in the largest amount next to iron. Most zinc ions in cells strongly couple to proteins and are involved in the maintenance of structure or in the expression of function of the protein. Various reports have been also made on the physiological role of free zinc ions, which are present in the cell in a very small quantity (generally at a level of μM or lower). In particular, zinc ions are considered to be significantly involved in one type of cell death, i.e., apoptosis, and it is reported that zinc ions accelerate senile plaque formation in Alzheimer's disease.

A compound (a fluorescent probe for zinc), which specifically traps a zinc ion to form a complex and emits fluorescence upon the formation of the complex, has been conventionally used to measure zinc ions in tissue. For example, TSQ (Reyes, J. G., et al., Biol. Res., 27, 49, 1994), Zinquin ethyl ester (Tsuda, M. et al., Neurosci., 17, 6678, 1997), Dansylaminoethylcyclen (Koike, T. et al., J. Am. Chem. Soc., 118, 12686, 1996), and Newport Green (a catalog of Molecular Probe: "Handbook of Fluorescent Probes and Research Chemicals" 6th Edition by Richard P. Haugland pp. 531–540) have been used practically as fluorescent probes for zinc.

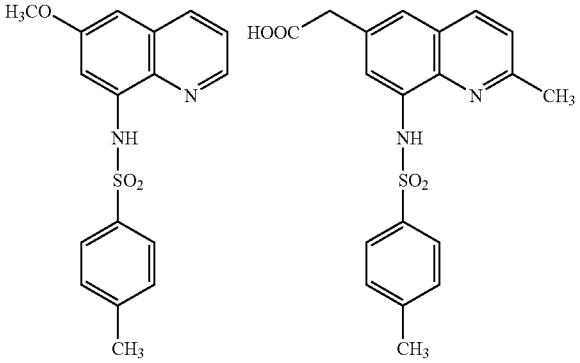

TSQ Zinquin

-continued

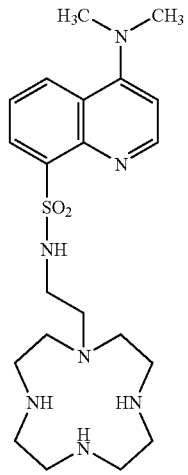

Dansylaminoethyl-cyclen

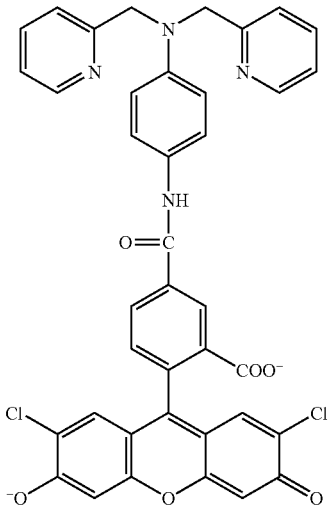

Newport Green

The measurement using TSQ, Zinquin, or Dansylaminoethylcyclen, however, requires the use of a short wavelength excitation light (an excitation wavelength of 367 nm, 368 nm, and 323 nm, respectively). Accordingly, when these fluorescent probes for zinc are used for measurement in living systems, the short wavelength excitation light may cause damages of cells (Saibou Kougaku (Cell Technology), 17, pp. 584–595, 1998). A problem also arises that the measurement may be readily influenced by autofluorescence generated from cell systems, per se (fluorescence emitted by NADH or flavin). Further, Dansylaminoethylcyclen has a drawback in that the fluorescence intensity is significantly varied depending on different environments in which the agent exists at the time of measurement, e.g., differences in environments such as a type of a solvent, or extracellular, intracellular, or intramembrane water solubility or lipophilicity or the like (Tanpakushitsu*Kakusan*Kouso (Protein, Nucleic Acid and Enzyme), extra number, 42, pp. 171–176, 1997). TSQ has a problem in that even distribution in the whole cell is difficult due to its high lipophilicity. Newport Green has low affinity for zinc ions and fails to achieve practical measurement sensitivity, although the agent enables measurement with a long wavelength excitation light. Therefore, the development of a fluorescent probe for zinc has been desired that can measure zinc ions with high sensitivity without damaging cells.

DISCLOSURE OF THE INVENTION

An object of the present invention is to provide a compound or a salt thereof which can be used as a highly sensitive fluorescent probe for zinc. More specifically, the object of the present invention is to provide a compound usable as a fluorescent probe for zinc, which can specifically trap zinc ions and has an excellent fluorescence intensity of a complex after the trap, and which can measure fluorescence with a long wavelength excitation light. Another object of the present invention is to provide a fluorescent probe for zinc comprising a compound having the above characteristics and a method for measuring zinc ions by using said fluorescent probe for zinc.

The inventors of the present invention have conducted various studies to achieve the foregoing objects. As a result, they found that a compound having a cyclic amine or a polyamine as a substituent has high specificity with zinc ions, and by trapping zinc ions, the compound forms a complex which emits strong fluorescence with a excitation light in longer wavelength range (Japanese Patent Application No. (Hei) 11-40325). The inventors have further conducts studies and found that a compounds represented by general formula (I) can form a complex with zinc very rapidly and can emit strong fluorescence. They also found that the compounds represented by general formula (I) can react with zinc ions for a split second in the living organism to form a fluorescent complex when they are used as a fluorescent probe for zinc, thereby zinc in the living organism can be measured with very high accuracy and sensitivity. The present invention was achieved on the basis of these findings.

The present invention thus provides a compound represented by general formula (IA) or (IB) or a salt thereof:

(IA)

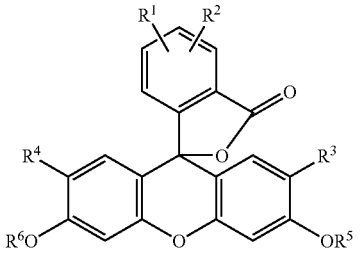

(IB)

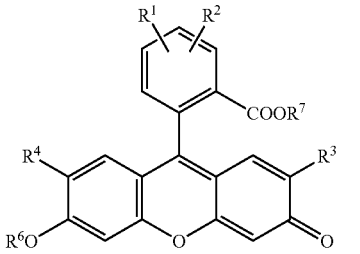

wherein $R^1$ and $R^2$ independently represent a hydrogen atom or a group represented by formula (A):

(A)

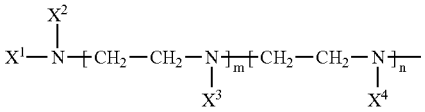

wherein $X^1$, $X^2$, $X^3$, and $X^4$ independently represent a hydrogen atom, an alkyl group, a 2-pyridylmethyl group, or a protective group for an amine group, and m and n independently represent 0 or 1, provided that $R^1$ and $R^2$ do not simultaneously represent hydrogen atoms; $R^3$ and $R^4$ independently represent a hydrogen atom or a halogen atom; $R^5$ and $R^6$ independently represent a hydrogen atom, an alkylcarbonyl group, or an alkylcarbonyloxymethyl group, and $R^7$ represents a hydrogen atom or an alkyl group.

As a preferred embodiment of the present invention, provided is a compound represented by general formula (II) or a salt thereof:

(II)

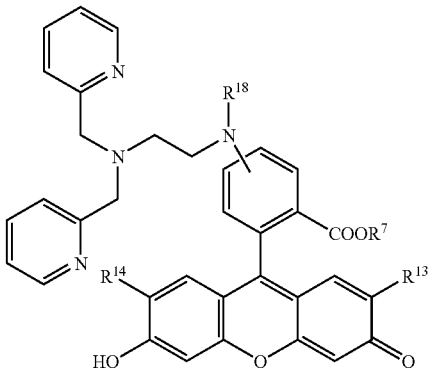

wherein $R^{13}$ and $R^{14}$ independently represent a hydrogen atom or a halogen atom; $R^{17}$ represents a hydrogen atom or an alkyl group; and $R^{18}$ represents a hydrogen atom or a protective group for an amino group. According to a preferred embodiment of the aforementioned invention, provided is the aforementioned compound or a salt thereof in which $R^{17}$ and $R^{18}$ independently represent hydrogen atoms. According to more preferred embodiment, provided is the aforementioned compound or a salt thereof in which a substituted amino group on the benzene ring binds in m-position or p-position relative to the group represented by —$COOR^{17}$.

Further, the present invention provides a compound represented by general formula (IIIA) or (IIIB) or a salt thereof:

(IIIA)

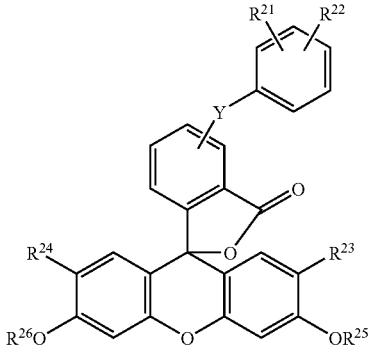

(IIIB)

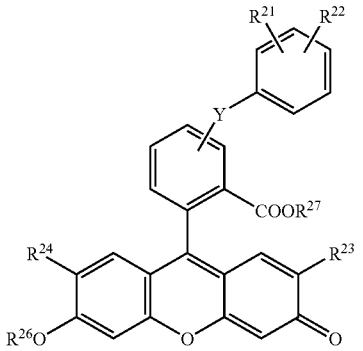

wherein $R^{21}$ and $R^{22}$ independently represent a hydrogen atom or a group represented by formula (B):

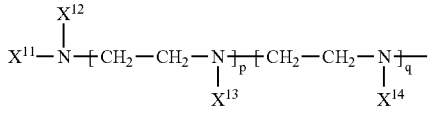

(B)

wherein $X^{11}$, $X^{12}$, $X^{13}$, and $X^{14}$ independently represent a hydrogen atom, an alkyl group, a 2-pyridylmethyl group, or a protective group for an amino group, and p and q are independently 0 or 1, provided that $R^{21}$ and $R^{22}$ do not simultaneously represent hydrogen atoms; Y represents —CO—NH— or —NH—CO—; $R^{23}$ and $R^{24}$ independently represent a hydrogen atom or a halogen atom; $R^{25}$ and $R^{26}$ independently represent a hydrogen atom, an alkylcarbonyl group, or an alkylcarbonyloxymethyl group; and $R^{27}$ represents a hydrogen atom or an alkyl group. According to a preferred embodiment of the invention, provides is the aforementioned compound in which Y on the benzene ring binds in m-position relative to the group represented by —$COOR^{27}$ (the corresponding carbonyl group when a lactone ring is formed).

From another aspect, the present invention provides a fluorescent probe for zinc which comprises a compound represented by the general formulas (I), (II), or (III) (excluding the compound wherein a protective group for an amino group is introduced) or a salt thereof; and a zinc complex constituted by a compound represented by the general formula (I), (II), or (III) (excluding the compound wherein a protective group for an amino group is introduced) or a salt thereof together with a zinc ion. The aforementioned fluorescent probe for zinc can be used for measuring zinc ions in tissues or cells.

From further aspect of the present invention, provided are a method for measuring zinc ions wherein a compound represented by the general formula (I), (II), or (III) (excluding the compound wherein a protective group for an amino group is introduced) or a salt thereof is used as a fluorescent probe for zinc; a method for measuring zinc ions which comprises the steps of: (a) reacting a compound represented by the general formula (I), (II), or (III) (excluding the compound wherein a protective group for an amino group is introduced) or a salt thereof with zinc ions; and (b) measuring fluorescence intensity of the zinc complex produced in the above step; and the use of a compound represented by the general formula (I), (II), or (III) (excluding the compound wherein a protective group for an amino group is introduced) or a salt thereof as a fluorescent probe for zinc.

The compound represented by the general formula (I), (II), or (III) (limited to the compound wherein a protective group for an amino group is introduced) is useful as a synthetic intermediate for the aforementioned fluorescent probe for zinc.

BEST MODE FOR CARRYING OUT THE INVENTION

Figure 1:
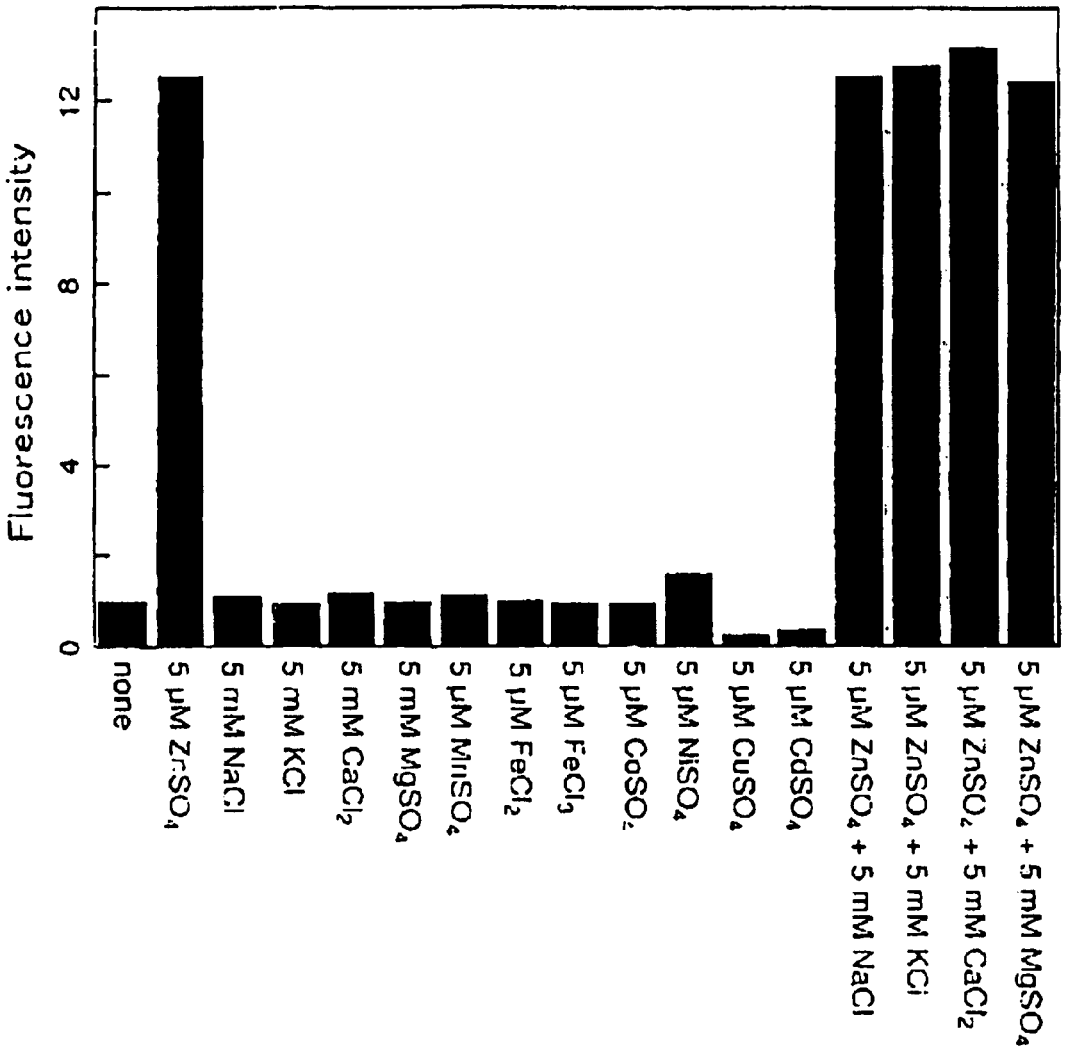
FIG. 1 shows that the fluorescent probe for zinc according to the present invention (Compound 6) has excellent zinc ion selectivity.

All the disclosures in the specification and claims of Japanese Patent Application No. 2000-50869 are incorporated herein by reference.

"An alkyl group" or an alkyl moiety of a substituent containing the alkyl moiety (for example, an alkylcarbonyl group or an alkylcarbonyloxymethyl group) used in the specification means, for example, a linear, branched, or cyclic alkyl group, or an alkyl group comprising a combination thereof having 1 to 12 carbon atoms, preferably 1 to 6 carbon atoms, and more preferably 1 to 4 carbon atoms. More specifically, a lower alkyl group (an alkyl group having 1 to 6 carbon atoms) is preferred as an alkyl group. Examples of the lower alkyl groups include methyl group, ethyl group, n-propyl group, isopropyl group, cyclopropyl group, n-butyl group, sec-butyl group, isobutyl group, tert-butyl group, cyclopropylmethyl group, n-pentyl group, and n-hexyl group. When "a halogen atom" is referred to, the term means any of a fluorine atom, a chlorine atom, a bromine atom, or an iodine atom, and preferably means a fluorine atom, a chlorine atom, or a bromine atom.

Types of protective groups for amino groups are not particularly limited. For example, a p-nitrobenzenesulfonic acid group, a trifluoroacetyl group, and a trialkylsily group can be suitably used. As for the protective groups for amino groups, reference can be made to, for example, "Protective Groups in Organic Synthesis," (T. W. Greene, John Wiley & Sons, Inc. (1981)).

In the general formulas (IA) and (IB), the positions of $R^1$ and $R^2$ substituted on the benzene ring are not particularly limited. When $R^2$ is a hydrogen atom, $R^1$ may preferably bind in Meta-position or para-position relative to the group represented by —$COOR^7$ (or corresponding carbonyl group when a lactone ring is formed). The position of an amino group substituted on the benzene ring in general formula (II) is not particularly limited. Meta-Position or para-position relative to the group represented by —$COOR^{17}$ is preferred. In the general formulas (IIIA) and (IIIB), the position of Y substituted on the benzene ring is not particularly limited. Y may preferably bind in meta-position relative to the group represented by —$COOR^{27}$ (or corresponding carbonyl group when a lactone ring is formed).

In the compounds represented by the general formulas (IA) and (IB), either of $R^1$ and $R^2$ is preferably a hydrogen atom and the other is preferably a group represented by formula (A). In the group represented by the formula (A), from $X^1$ to $X^4$, preferably $X^1$ and $X^2$, independently represent a 2-pyridylmethyl group. In the compounds represented by the general formulas (IA) and (IB), preferably, m is 0, n is 1, and $X^4$ is hydrogen atom. In the above particular compounds, both of $X^1$ and $X^2$ are preferably 2-pyridylmethyl group. $R^5$ and $R^6$ are preferably hydrogen atoms, and $R^5$ and $R^6$ are preferably acetyl groups or acetoxymethyl groups for imaging application. It is preferred that both of $R^3$ and $R^4$ are hydrogen atoms or chlorine atoms. $R^7$ is preferably a hydrogen atom.

In the compound represented by general formula (II), both of $R^{13}$ and $R^{14}$ are preferably hydrogen atoms or chlorine atoms. $R^{17}$ and $R^{18}$ are preferably hydrogen atoms.

In the compounds represented by the general formulas (IIIA) and (IIIB), either of $R^{21}$ and $R^{22}$ is preferably a hydrogen atom and the other is preferably a group represented by formula (B). In the group represented by the formula (B), from $X^{11}$ to $X^{14}$, preferably $X^{11}$ and $X^{12}$, independently represent a 2-pyridylmethyl group. In the compounds represented by the general formulas (IIIA) and (IIIB), preferably, p is 0, q is 1, and $X^{14}$ is a hydrogen atom. In the above particular compounds, both of $X^{11}$ and $X^{12}$ are preferably 2-pyridylmethyl groups. Both of $R^{23}$ and $R^{24}$ are preferably hydrogen atoms or chlorine atoms. $R^{25}$ and $R^{26}$ are preferably hydrogen atoms, and $R^{25}$ and $R^{26}$ are preferably acetyl groups or acetoxymethyl groups for imaging application. $R^{27}$ is preferably a hydrogen atom.

The compounds of the present invention represented by the general formulas (I) to (III) can exist as acid addition salts or base addition salts. Examples of the acid addition salts include: mineral acid salts such as hydrochloride, sulfate, and nitrate; and organic acid salts such as methanesulfonate, p-toluenesulfonate, oxalate, citrate, and tartrate. Examples of the base addition salts include: metal salts such as sodium salts, potassium salts, calcium salts, and magnesium salts; ammonium salts; and organic amine salts such as triethylamine salts. In addition, salts of amino acids such as glycine may be formed. The compounds or salts thereof according to the present invention may exit as hydrates or solvates, and these substances fall within the scope of the present invention.

the compounds of the present invention represented by general formulas (IA), (IB), (II), (IIIA), and (IIIB) may have one or more asymmetric carbons depending on the types of the substituents. Stereoisomers such as optically active substances based on one or more asymmetric carbons and diastereoisomers based on two or more asymmetric carbons, as well as any mixtures of the stereoisomers, racemates and the like fall within the scope of the present invention. When $R^7$, $R^{17}$, or $R^{27}$ is hydrogen atom, a carboxyl group may form a lactone, and such structural isomers also fall within the scope of the present invention. A compound represented by general formula (IA) in which $R^5$ is a hydrogen atom and a compound represented by general formula (IB) in which $R^7$ is a hydrogen atom are tautomers, and similarly, a compound represented by general formula (IIIA) in which $R^{25}$ is a hydrogen atom and a compound represented by general formula (IIIB) in which $R^{27}$ is a hydrogen atom are tautomers. One of ordinary skill in the art would readily recognize the existence of the tautomers as explained above, and therefore, it should be understood that any of these tautomers fall within the scope of the present invention.

Methods for preparing typical compounds of the present invention are shown in the following schemes. The preparation methods shown in the schemes are more specifically detailed in the examples of the specification. Accordingly, one or ordinary skill in the art can prepare any of the compounds according to the present invention represented by the general formula by suitably choosing starting reaction materials, reaction conditions, reagents and the like based on these explanations, and optionally modifying and altering these methods. 4-Aminofluorescein, 5-aminofluorescein, and 6-aminofluorescein, which can be used as starting compounds, can be prepared by methods described in, for example, "Yuuki Gousei Kagaku (Synthetic Organic Chemistry) IX," (Tetsuji Kametani, Nankodo Co., Ltd., p. 215 (1977)).

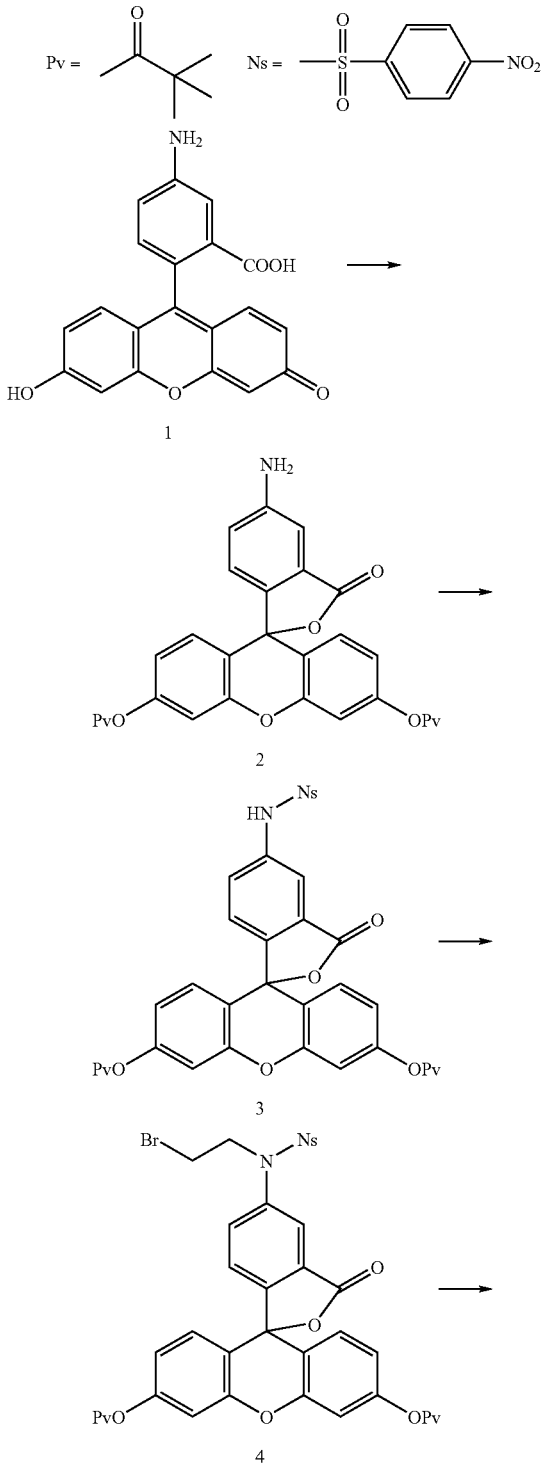

-continued
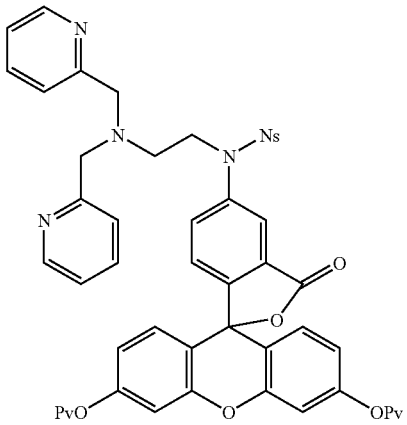
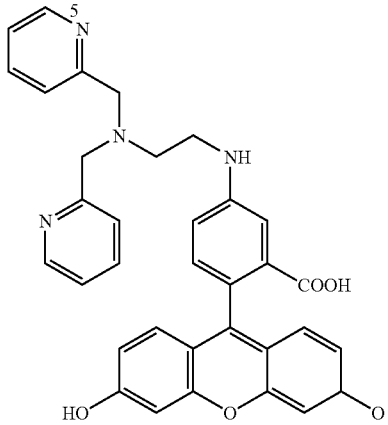
6
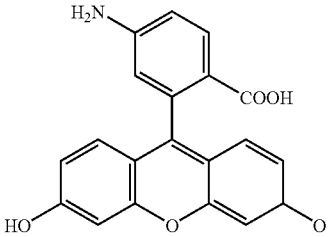
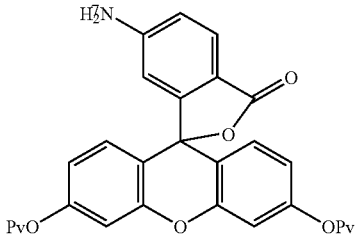
8
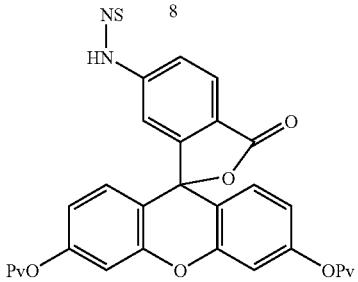
9
-continued
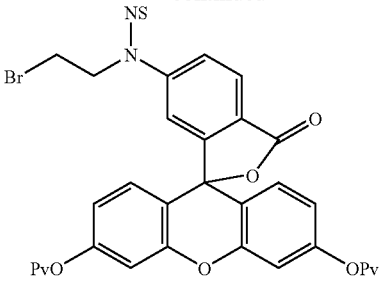
10
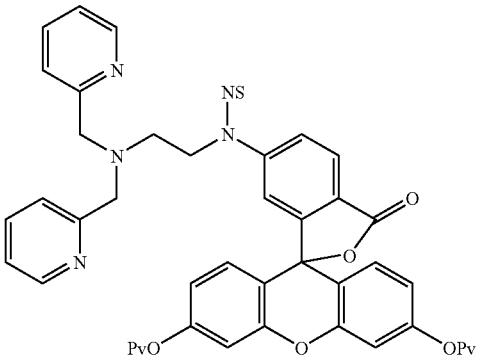
11
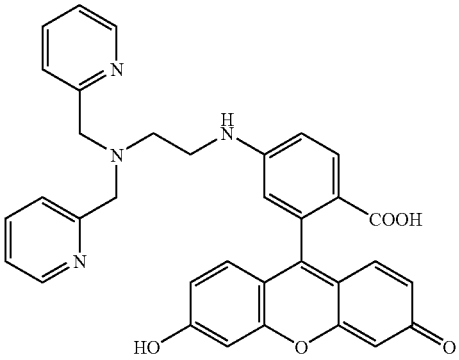
12
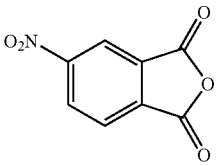
13
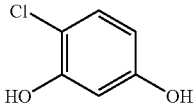
14
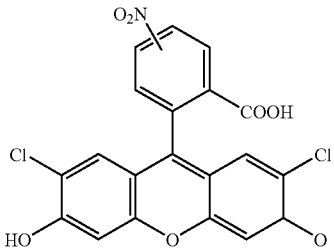
15

-continued
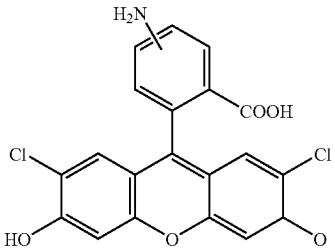
16
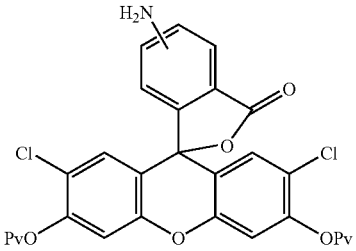
17
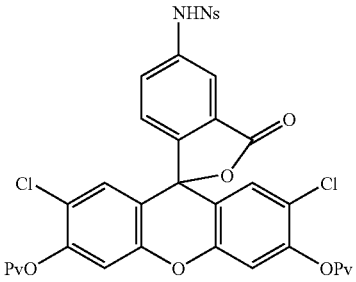
18
+
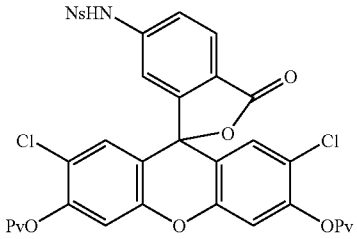
18′
-continued
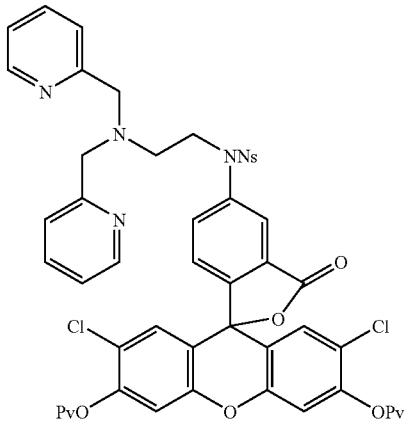
20
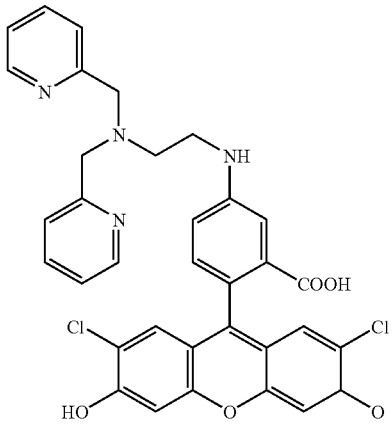
21
18′ →
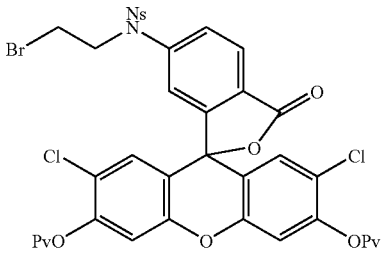
19′
18 →
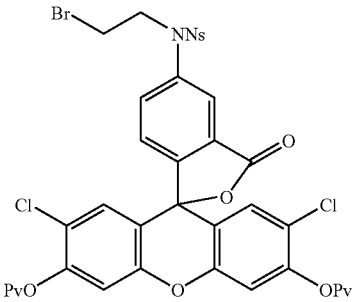
19
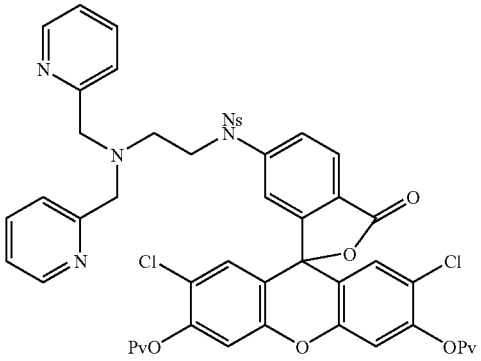
20′

-continued

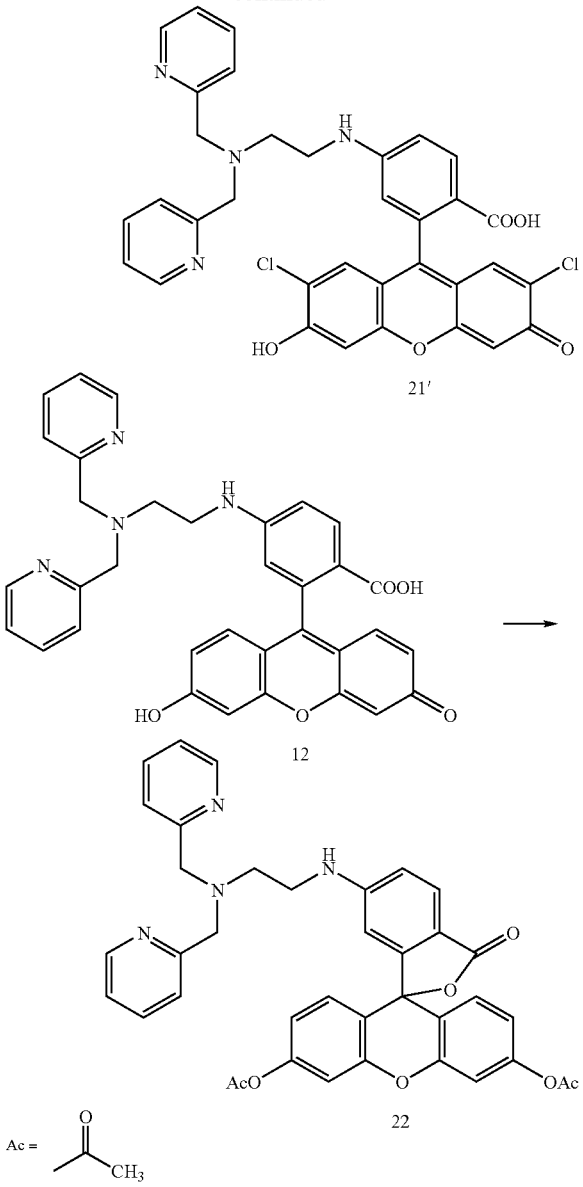

The compound represented by the general formula (III) can be prepared by, for example, a method shows in the following scheme by using a commercially available compound and the like as a reagent and a starting reaction material.

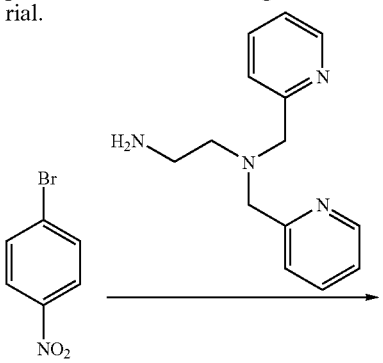

-continued

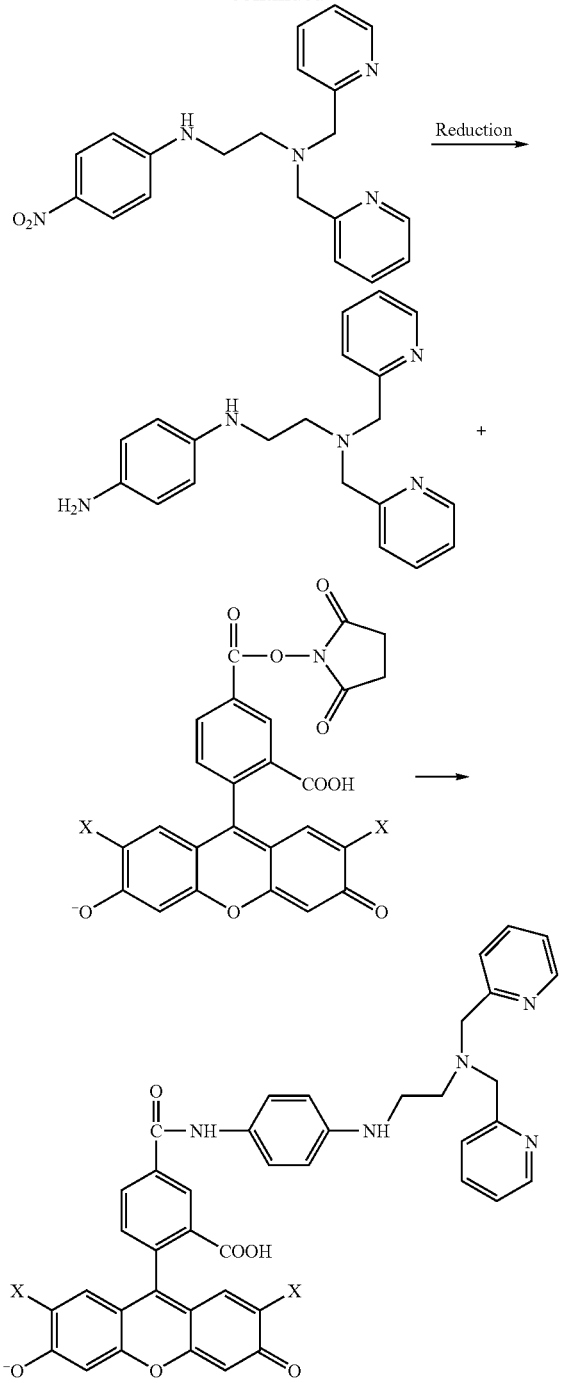

The compounds of the present invention represented by the general formulas (I), (II), and (III) (excluding a compound having a protective group for an amino group) or salts thereof are useful as fluorescent probes for zinc. The compounds of the present invention represented by the general formulas (I), (II), or (III) or salts thereof, per se, do not emit strong fluorescence, whilst they come to emit strong fluorescence after the formation of zinc complexes by trapping zinc ions. The above compounds or salts thereof are featured that they can specifically trap zinc ions and form the complex very rapidly. In addition, the formed zinc complexes is featured to emit strong fluorescence under a long wavelength excitation light which does not cause any damage to living tissues or cells. Accordingly, the compounds of the present invention represented by the general formula (I), (II), or (III) or salts thereof are very useful as a fluorescent probes for zinc for measurement of zinc ions in living cells or living tissues under a physiological condition. The term "measurement" used in the specification should be construed in its broadest sense, including quantitative and qualitative measurement.

The method for using the fluorescent probe for zinc according to the present invention is not particularly limited, and the probe can be used in the same manner as conventional zinc probes. In general, a substance selected from the group consisting of the compounds represented by the general formula (I) and salts thereof is dissolved in an aqueous medium such as physiological saline or a buffered solution, or in a mixture of the aqueous medium and a water-miscible organic solvent such as ethanol, actone, ethylene glycol, dimethysulfoxide, and dimethylformamide, and then the resultant solution is added to a suitable buffered solution containing cells or tissues and a fluorescence spectrum can be measured.

For example, the zinc complexes of Compound 6 and Compound 12 shown in the above scheme have the excitation wavelengths of 491 nm and 492 nm, and the fluorescence wavelengths of 513 nm and 514 nm, respectively. When the compound is used at a concentration of about 1 to 10 μM, zinc ions with a concentration of 10 μM or below can be measured. The fluorescent probe for zinc according to the present invention may be combined with a suitable additive to use in the form of a composition. For example, the fluorescent probe for zinc can be combined with additives such as a buffering agent, a solubilizing agent, and a pH modifier.

Compound 22, for example, has lipophilicity such a degree that it can easily permeate cell membranes. After Compound 22 permeates cell membranes, the compound is hydrolyzed by an esterase present in the cytoplasm, thereby Compound 12 is produced. Compound 12 can hardly permeate cell membranes due to its water-solubility, and for this reason, Compound 12 can be retained intracellularly for a prolonged period of time. Accordingly, Compound 22 is very useful for measurement of zinc ions existing in an individual cell.

EXAMPLES

The present invention will be more specifically explained with reference to the following examples. However, the scope of the present invention is not limited to these examples. The compound number in the examples correspond to those used in the above schemes.

Example 1

Synthesis of Compound 6

Cesium carbonate (5.2 g, 16 mmol) was added to a solution of 4-aminofluorescein (1) (2.5 g, 7.2 mmol) dissolved in 50 ml of dimethylformamide. Subsequently, pivaloyl anhydride (3.1 ml, 15 mmol) was added to this solution, and the mixture was stirred at room temperature for 1 hour. The reaction solution was filtered using a Kiriyama funnel, and dimethylformamide was evaporated under reduced pressure. The residue was purified by column chromatography on silica gel to obtain 3.6 g of Compound 2 (white solid, yield: 97%).

$^1$H-NMR ($CDCl_3$, 300 MHz): 7.19 (m, 1H), 7.02 (d, 2H, J=2.4), 6.93–6.94 (m, 2H), 6.88 (d, 2H, J=8.7), 6.77 (dd, 2H, J=8.7, 2.4), 4.06 (br, 2H), 1.34 (s, 18H)

MS (FAB): 516 ($M^+$+1)

m.p.: 206–208° C. (recrystallized from methanol)

Compound 2 (1.0 g, 2.0 mmol) was dissolved in 15 ml of pyridine and the solution was added with 4-nitrobenzenesulfonyl chloride (1.2 g, 5.3 mmol), and the mixture was then stirred at room temperature for 6 hours. Pyridine was evaporated under reduced pressure, and the residue was dissolved in 25 ml of ethyl acetate. The ethyl acetate solution was washed with 2N hydrochloric acid and saturated brine, and was then dried over sodium sulfate. After ethyl acetate was evaporated under reduced pressure, purification was carried out by column chromatography on silica gel to obtain 1.2 g of Compound 3 (white solid, yield: 88%).

$^1$H-NMR ($CDCl_3$, 300 MHz): 8.33 (d, 2H, J=9.0), 8.05 (d, 2H, J=9.0), 7.69 (d, 1H, J=2.2), 7.45 (dd, 1H, J=8.2, 2.2), 7.07 (d, 1H, J=8.2), 7.06–7.04 (m, 2H), 6.77–6.74 (m, 4H), 1.36 (s, 18H)

MS (FAB): 701($M^+$+1)

m.p.: 245–247° C. (recrystallized from ethyl acetate+n-hexane)

Cesium carbonate (0.48 g, 1.5 mmol) and 1,2-dibromoethane (1.3 ml, 14 mmol) were added to a solution of Compound 3 (0.97 g, 1.4 mmol) dissolved in 25 ml of dimethylformamide, and the mixture was stirred at 60° C. for 20 hours. Dimethylformamide was evaporated under reduced pressure and dissolved in 50 ml of ethyl acetate. The ethyl acetate solution was washed with water and saturated brine, and then dried over sodium sulfate. After ethyl acetate was evaporated under reduced pressure, purification was carried out by column chromatography on silica gel to obtain 0.78 g of Compound 4 (white solid, yield: 70%).

$^1$H-NMR ($CDCl_3$, 300 MHz): 8.38 (d, 2H, J=9.0), 7.86 (d, 2H, J=9.0), 7.76 (d, 1H, J=2.0), 7.45 (dd, 1H, J=8.0, 2.0), 7.17 (d, 1H, J=8.0), 7.08 (m, 2H), 6.85–6.84 (m, 4H), 4.01 (t, 2H, J=6.8), 3.45 (t, 2H, J=6.8), 1.37 (s, 18H)

MS (FAB): 807, 809 ($M^+$+1)

m.p.: 280–281° C. (recrystallized from acetonitrile)

Compound 4 (0.10 g, 0.13 mmol) was suspended in 4 ml of acetonitrile, and the suspension was added with potassium iodide (55 mg, 0.33 mmol), potassium carbonate (43 mg, 0.31 mmol), and 2,2'-dipicolylamine (78 mg, 0.39 mmol), and then the mixture was refluxed for 14 hours. After acetonitrile was evaporated under reduced pressure, the product was dissolved in an aqueous solution of 2N sodium carbonate, followed by extraction with methylene chloride. The methylene chloride layer was washed with saturated brine and was then dried over sodium sulfate. Methylene chloride was evaporated under reduced pressure, followed by purification by column chromatography on silica gel to obtain 80 mg of Compound 5 (light yellow oil, yield: 69%).

$^1$H-NMR ($CDCl_3$, 300 MHz): 8.47–8.45 (m, 2H), 8.32 (d, 2H, J=9.0), 7.77 (d, 2H, J=9.0), 7.69–7.61 (m, 3H), 7.61 (d, 2H, J=7.9), 7.27–7.23 (m, 1H), 7.14 (m, 2H), 7.07 (d, 2H, J=2.2), 6.99 (d, 1H, J=8.0), 6.82 (dd, 2H, J=8.6, 2.2), 6.72 (d, 2H, J=8.6), 3.82 (s, 4H), 3.82 (m, 2H), 2.72 (t, 2H, J=6.4), 1.37 (s, 18H)

MS (FAB): 926 ($M^+$+1)

Potassium carbonate (26 mg, 0.19 mmol) and thiophenol (12 μl, 0.12 mmol) were added to a solution of Compound 5 (34 mg, 37 μmol) dissolved in 4 ml of dimethylformamide, and the mixture was stirred at room temperature for 3 hours. A solution of potassium hydroxide (70 mg, 1.2 mmol), dissolved in 1 ml of methanol and 1 ml of water, was added to the reaction mixture, and the mixture was stirred at room temperature for 20 hours. After 2 ml of 2N hydrochloric acid was added to the mixture, the solvent was evaporated under reduced pressure. The product was suspended in 10 ml of ethanol and filtered, and then the ethanol was evaporated under reduced pressure. The residue was purified by reversed-phase HPLC to obtain 15 mg of Compound 6 (brown solid, yield: 70%).

$^1$H-NMR ($CD_3OD$, 300 MHz): 8.61–8.59 (m, 2H), 8.04–7.98 (m, 2H), 7.63 (d, 2H, J=7.9), 7.51–7.46 (m, 2H), 7.14 (d, 1H, J=2.0), 7.02 (d, 2H, J=9.0), 6.95–6.87 (m, 4H), 6.79 (dd, 2H, J=9.0, 2.4), 4.46 (s, 4H), 3.50 (t, 2H, J=6.0), 3.25 (m, 2H)

MS (FAB): 573 ($M^+$+1)

Example 2

Synthesis of Compound 12

Compound 8 (4.4 g) was obtained from 5-aminofluorescein (7) (3.5 g, 10 mmol) in the same manner as that of the synthesis of Compound 2 (white solid, yield: 84%).

$^1$H-NMR ($CDCl_3$, 300 MHz): 7.77 (d, 1H, J=7.9 ), 7.01 (d, 2H, J=2.0), 6.95 (d, 2H, J=8.6), 6.80–6.75 (m, 3H), 6.22 (d, 1H, J=1.7), 4.21 (br, 2H), 1.36 (s, 18H)

MS (FAB): 516 ($M^+$+1)

m.p.: 161–163° C. (recrystallized from methanol)

Compound 9 (4.1 g) was obtained from Compound 8 (3.6 g, 6.9 mmol) in the same manner as that of the synthesis of Compound 3 (white solid, yield: 84%).

$^1$H-NMR ($CDCl_3$, 300 MHz): 8.61 (br, 1H), 8.20 (d, 2H, J=9.0), 7.88 (d, 1H, J=8.3), 7.81 (d, 2H, J=9.0), 7.33–7.29 (m, 1H), 7.05 (d, 2H, J=2.2), 6.84 (d, 1H, J=1.8), 6.74 (dd, 2H, J=8.6, 2.2), 6.69 (d, 2H, J=8.6), 1.38 (s, 18H)

MS (FAB): 701 ($M^+$+1)

m.p.: 189–191° C. (recrystallized from ethyl acetate+n–hexane)

Compound 10 (0.35 g) was obtained from Compound 9 (0.51 g, 0.73 mmol) in the same manner as that of the synthesis of Compound 4 (white solid, yield: 60%).

$^1$H-NMR ($CDCl_3$, 300 MHz): 8.11 (d, 2H, J=9.0), 8.10–8.09 (m, 1H), 7.71 (dd, 1H, J=8.2, 1.8), 7.56 (d, 2H, J=9.0), 7.02 (d, 2H, J=2.2), 6.86 (dd, 2H, J=8.6, 2.2), 6.79 (d, 2H, J=8.6), 6.43 (d, 1H, J=1.8), 3.85 (t, 2H, J=6.6), 3.40 (t, 2H, J=6.6), 1.38 (s, 18H)

MS (FAB): 807, 809 ($M^+$+1)

m.p.: 268–269° C. (recrystallized from acetonitrile)

Compound 11 (0.27 g) was obtained from Compound 10 (0.31 g, 0.38 mmol) in the same manner as that of the synthesis of Compound 5 (light yellow solid, yield: 75%).

$^1$H-NMR ($CDCl_3$, 300 MHz): 8.45–8.42 (m, 2H), 8.06 (d, 2H, J=9.0), 7.96 (d, 1H, J=8.3), 7.64–7.59 (m, 2H), 7.52 (d, 2H, J=9.0), 7.53–7.50 (m, 1H), 7.33 (d, 2H, J=7.7), 7.17 (d, 2H), 7.00 (d, 2H, J=2.2), 6.78 (dd, 2H, J=8.6, 2.2), 6.64 (d, 2H, J=8.6), 6.48 (d, 1H, J=1.3), 3.71 (s, 4H), 3.67 (t, 2H, J=6.2), 2.67 (t, 2H, J=6.2), 1.37 (s, 18H)

MS (FAB): 926 ($M^+$+1)

m.p.: 146–148° C. (recrystallized from methanol)

Compound 12 (6.6 mg) was obtained from Compound 11 (20 mg, 22 μmol) in the same manner as that of the synthesis of Compound 6 (brown solid, yield: 53%).

$^1$H-NMR ($CD_3OD$, 300 MHz): 8.44–8.42 (m, 2H), 7.94–7.88 (m, 2H), 7.60 (d, 1H, J=8.4), 7.49 (d, 2H, J=7.9), 7.45–7.41 (m, 2H), 6.71 (br, 1H), 6.65 (d, 2H, J=2.4), 6.61 (d, 2H, J=8.8), 6.51 (dd, 2H, J=8.8, 2.4), 6.02 (d, 1H, J=1.8), 4.30 (s, 4H), 3.28 (t, 2H, J=6.0), 3.03 (t, 2H, J=6.0)

MS (FAB): 573 ($M^+$+1)

Example 3

Synthesis of Compound 15

4-Nitrophthalic anhydride (13) (16 g, 84 mmol) and 4-chlororesorcinol (14) (24 g, 0.17 mol) were dissolved in 250 ml of methanesulfonic acid, and the mixture was stirred under argon at 80° C. for 60 hours. The mixture was cooled to room temperature and then added in small portions to 1.4 L of ice water. The precipitated solid was collected by filtration to obtain 37 g of Compound 15 (quantitative yield).

Synthesis of Compound 16

Compound (15) (20 g, 45 mmol) was suspended in 700 ml of water, and the suspension was added with sodium sulfate nonahydrate (54 g, 0.23 mol) and sodium hydrosulfide n-hydrate (20 g, 0.25 mol, about 70% of sodium hydrosulfide), and the mixture was refluxed under argon for 20 hours. After cooled to room temperature, the mixture was added with hydrochloric acid to adjust pH at 3 to 4. The precipitated solid was collected by filtration to obtain 19 g of Compound (16) (quantitative yield).

Synthesis of Compound 17

Compound (17) (3.9g) was obtained from Compound (16) (4.4 g, 11 mmol) in the same manner as that of the synthesis of Compound (2) (yield: 62%).

MS (FAB): 584, 586, 588 ($M^+$+1)

Synthesis of Compounds 18 and 18'

Compound (18) (1.9 g) and 1.8 g of Compound (18') were obtained from Compound (17) (3.8 g, 6.5 mmol) in the same manner as that of the synthesis of Compound (3) (yield: 38% for Compound (18); 35% for Compound (18')).

Compound (18):

$^1$H-NMR ($CDCl_3$, 300 MHz): 8.38 (d, 2H, J=8.7), 8.07 (d, 2H, J=8.7), 7.72 (d, 1H, J=2.1), 7.48 (dd, 1H, J=8.1, 2.1), 7.12 (d, 1H, J=8.1), 7.11 (s, 2H), 6.77 (s, 2H), 1.40 (s, 18H)

MS (FAB): 769, 771, 773 ($M^+$+1)

Compound (18'):

$^1$N-NMR ($CDCl_3$, 300 MHz): 8.26 (d, 2H, J=8.6), 7.93 (d, 1H, J=8.4), 7.84 (d, 2H, J=8.6), 7.27 (dd, 1H, J=8.4, 2.0), 7.13 (s, 2H), 6.99 (d, 1H, J=2.0), 6.75 (s, 2H), 1.42 (s, 18H)

MS (FAB): 769, 771, 773 ($M^+$+1)

Synthesis of Compound 19

Compound (19) (1.2 g) was obtained from Compound (18) (1.5 g, 2.0 mmol) in the same manner as that of the synthesis of Compound (4) (yield: 66%).

$^1$H-NMR ($CDCl_3$, 300 MHz): 8.39 (d, 2H, J=9.0), 7.85 (d, 2H, J=9.0), 7.79 (d, 1H, J=2.0), 7.51 (dd, 1H, J=8.2, 2.0), 7.18 (d, 1H, J=8.2), 7.14 (s, 2H), 6.89(s, 2H), 4.06 (t, 2H, J=6.8), 3.50 (t, 2H, J=6.8), 1.40 (s, 18H)

MS (FAB): 875, 877, 879, 881 ($M^+$+1)

Synthesis of Compound 19'

Compound (19') (0.70 g) was obtained from Compound (18') (1.5 g, 2.0 mmol) in the same manner as that of the synthesis of Compound (4) (yield: 40%).

$^1$H-NMR ($CDCl_3$, 300 MHz): 8.19 (d, 2H, J=9.0), 8.13 (d, 1H, J=8.3), 7.70 (brd, 1H), 7.62 (d, 2H, J=9.0), 7.11 (s, 2H), 6.84 (s, 2H), 6.63 (d, 1H, J=1.8), 3.94(t, 2H, J=6.4), 3.46 (t, 2H, J=6.4), 1.41 (s, 18H)

MS (FAB): 875, 877, 879, 881 ($M^+$+1)

Synthesis of Compound 20

Compound (20) (0.56 g) was obtained from Compound (19) (1.0 g, 1.1 mmol) in the same manner as that of the synthesis of Compound (5) (yield: 49%).

$^1$H-NMR ($CDCl_3$, 300 MHz): 8.50–8.47 (m, 2H), 8.33 (d, 2H, J=8.7), 7.76 (d, 2H, J=8.7), 7.70–7.60 (m, 3H), 7.46 (d, 2H, J=7.9), 7.32 (brd, 1H, J=8.3), 7.16–7.12 (m, 2H), 7.14 (s, 2H), 7.00 (d, 1H, J=8.3), 6.79 (s, 2H), 3.87 (t, 2H, J=6.0), 3.83 (s, 4H), 2.76 (t, 2H, J=6.0), 1.41 (s, 18H)

MS (FAB): 994, 996, 998 ($M^+$+1)

Synthesis of Compound 20 '

Compound (20') (75 mg) was obtained from Compound (19') (0.20 g, 0.23 mmol) in the same manner as that of the synthesis of Compound (5) (yield: 33%).

$^1$H-NMR ($CDCl_3$, 300 MHz): 8.43–8.41 (m, 2H), 8.17 (d, 2H, J=9.0), 7.97 (d, 1H, J=8.3), 7.63–7.57 (m, 2H), 7.56 (d, 2H, J=9.0), 7.49 (brd, 1H, J=8.3), 7.31 (d, 2H, J=7.7), 7.16–7.12 (m, 2H), 7.08 (s, 2H), 6.79 (s, 2H), 6.72 (d, 2H, J=1.1), 3.74 (t, 2H, J=6.2), 3.71 (s, 4H), 2.74 (t, 2H, J=6.2), 1.40 (s, 18H)

MS (FAB): 994, 996, 998 ($M^+$+1)

Synthesis of Compound 21

Compound (21) (98 mg) was obtained from Compound (20) (0.26 g, 0.26 mmol) in the same manner as that of the synthesis of Compound (6) (yield: 35%).

$^1$H-NMR ($CD_3OD$, 300 MHz): 8.56 (brd, 2H, J=4.8), 7.98–7.91 (m, 2H), 7.57 (d, 2H, J=7.9), 7.46–7.41 (m, 2H), 6.94–6.81 (m, 3H), 6.73 (s, 2H), 6.56 (s, 2H), 4.48 (s, 4H), 3.50 (t, 2H, J=5.5), 3.29 (t, 2H, J=5.5)

MS (FAB): 641, 643, 645 ($M^+$+1)

Synthesis of Compound 21'

Compound (21') (58 mg) was obtained from Compound (20') (0.20 g, 0.20 mmol) in the same manner as that of the synthesis of Compound (6) (yield: 26%).

$^1$H-NMR ($CD_3OD$, 300 MHz): 8.45–8.43 (m, 2H), 7.93–7.88 (m, 2H), 7.58 (d, 1H, J=8.6), 7.50 (d, 2H, J=7.9), 7.45–7.41 (m, 2H), 6.72 (s, 2H), 6.73–6.88 (m, 1H), 6.58 (s, 2H), 6.01 (d, 1H, J=1.8), 4.30 (s, 4H), 3.27 (t, 2H, J=5.7), 3.06 (t, 2H, J=5.7)

MS (FAB): 641, 643, 645 ($M^+$+1)

Synthesis of Compound 22

Compound (12) (140 mg, 0.13 mmol) was suspended in 10 ml of acetonitrile, and the suspension was added with cesium carbonate (0.19 g, 0.30 mmol), and then with 28 μl of acetic anhydride portionwise. After the mixture was stirred at room temperature for 1 hour, the reaction mixture was filtered. The solvent was evaporated under reduced pressure, followed by purification by column chromatography on silica gel to obtain 79 mg of Compound (22) (yield: 94%).

$^1$H-NMR ($CDCl_3$, 300 MHz): 8.51–8.49 (m, 2H), 7.73 (d, 1H, J=8.4), 7.60–7.54 (m, 2H), 7.31 (d, 2H, J=7.7), 7.15–7.11 (m, 2H), 7.05 (d, 2H, J=2.2), 6.96 (d, 2H, J=8.6), 6.80 (dd, 2H, J=2.2, 8.6), 6.77–6.74 (m, 1H), 6.48 (br, 1H), 6.02 (d, 1H, J=1.7), 3.86 (s, 4H), 3.06 (br, 2H), 2.82 (t, 2H, J=5.1), 2.31 (s, 6H)

Example 4

Figure 2:
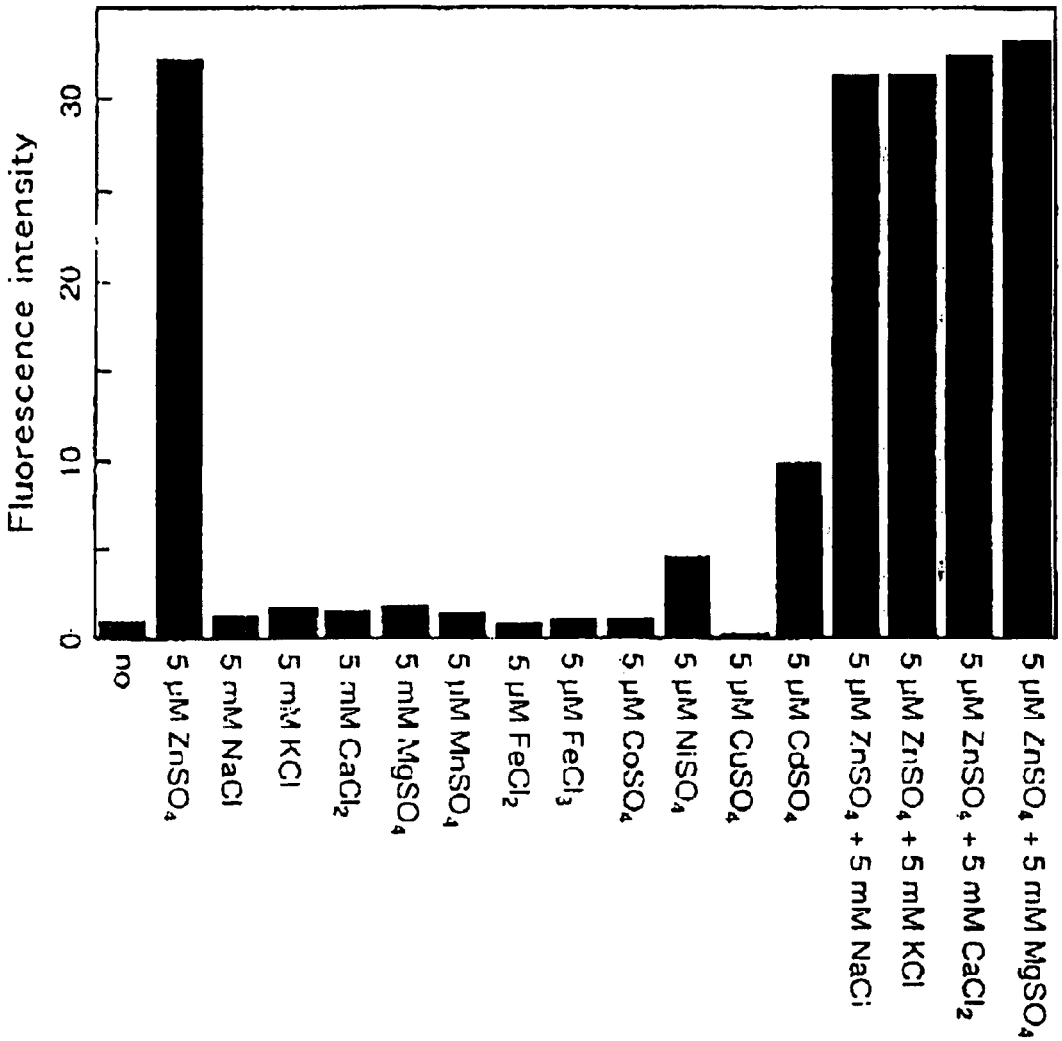
FIG. 2 shows that the fluorescent probe for zinc according to the present invention (Compound 12) has excellent zinc ion selectivity.
Figure 3:
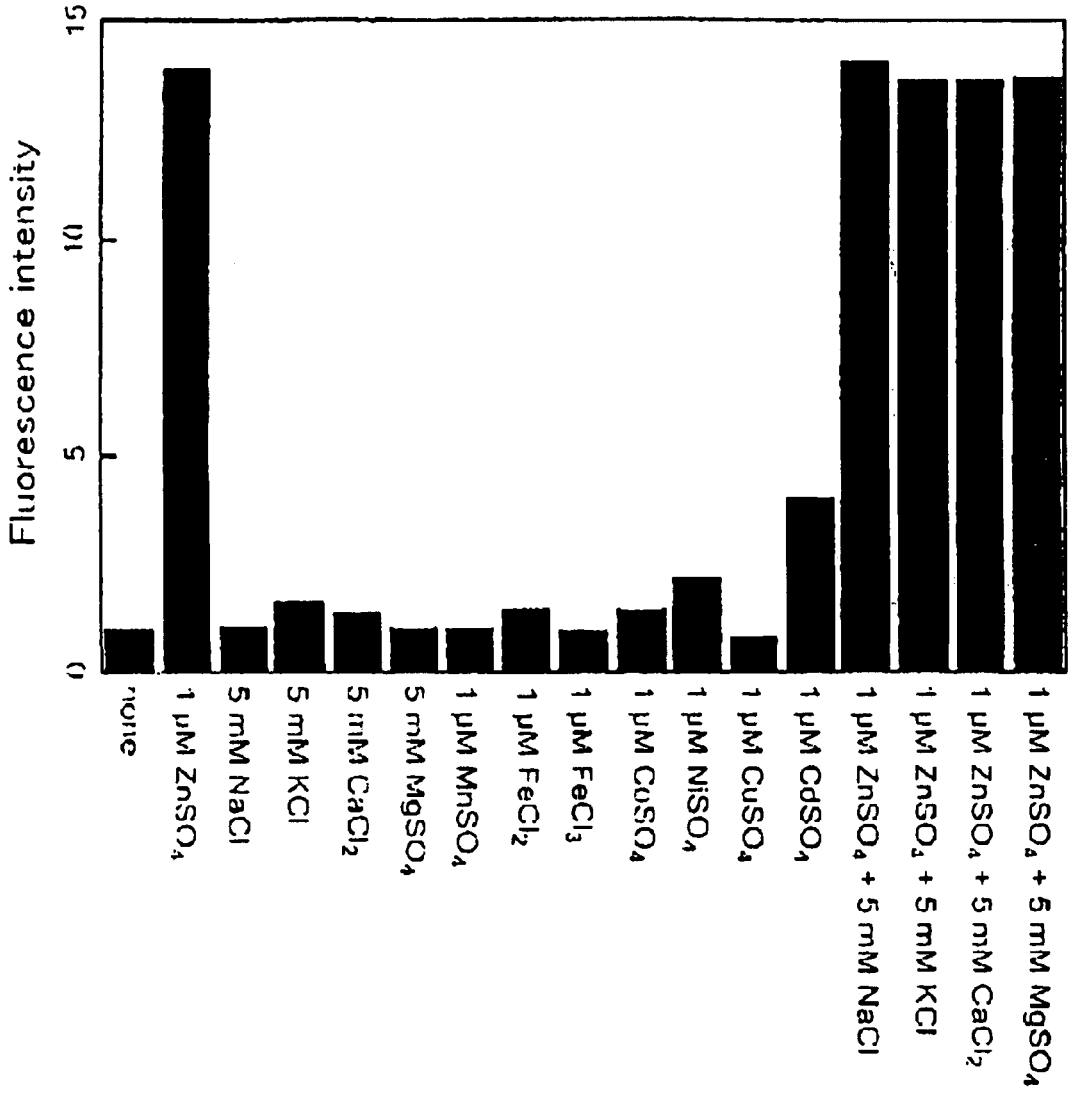
FIG. 3 shows that the fluorescent probe for Zinc according to the present invention (Compound 21) has excellent zinc ion selectivity.

Compound 6 obtained in Example 1 and Compound 12 obtained in Example 2 were used to evaluate selectivity for zinc ions. 5 μM of Compound 6 or Compound 12 was added in 100 mM HEPES buffer (pH 7.5) containing various metal ions (5 μM or 5 mM). The fluorescence intensity was measured at the excitation wavelength of 491 nm and the fluorescence wavelength of 513 nm for Compound 6, and the excitation wavelength of 492 nm and the fluorescence wavelength of 514 nm for Compound 12. The results are shown in FIG. 1 (Compound 6) and FIG. 2 (Compound 12). 1 μM of Compound 21 was added in 100 mM HEPES buffer (pH 7.5) containing various metal ions (1 μM or 5 mM), and the fluorescence intensity was measured at the excitation wavelength of 505 nm and the fluorescence wavelength of 522 nm. The results are shown in FIG. 3.

In the figures, the fluorescence intensities on the ordinate axis are shown as numerical values with addition of each metal ion relative to the fluorescence intensity without addition of metal ion which is taken as 1. It is clearly understood that Compound 6 and Compound 12 of the present invention have extremely high selectivity for zinc ions, and the compound give absolutely no increase of fluorescence intensity even in the presence of sodium ions, potassium ions, calcium ions, and magnesium ions at high concentration (5 mM), which exist in a living organism in large amounts. It is also clearly understood that these metal ions do not affect the increase in fluorescence intensity by zinc ions.

Compound 21 exhibited high selectively for zinc. In particular, the addition of sodium, potassium, calcium, and magnesium at high concentration (5 mM), which are metal ions present abundant in living organisms, gives almost no increase in fluorescence intensity. These metal ions did not affect the increase in fluorescence intensity caused by zinc.

Example 5

Figure 4:
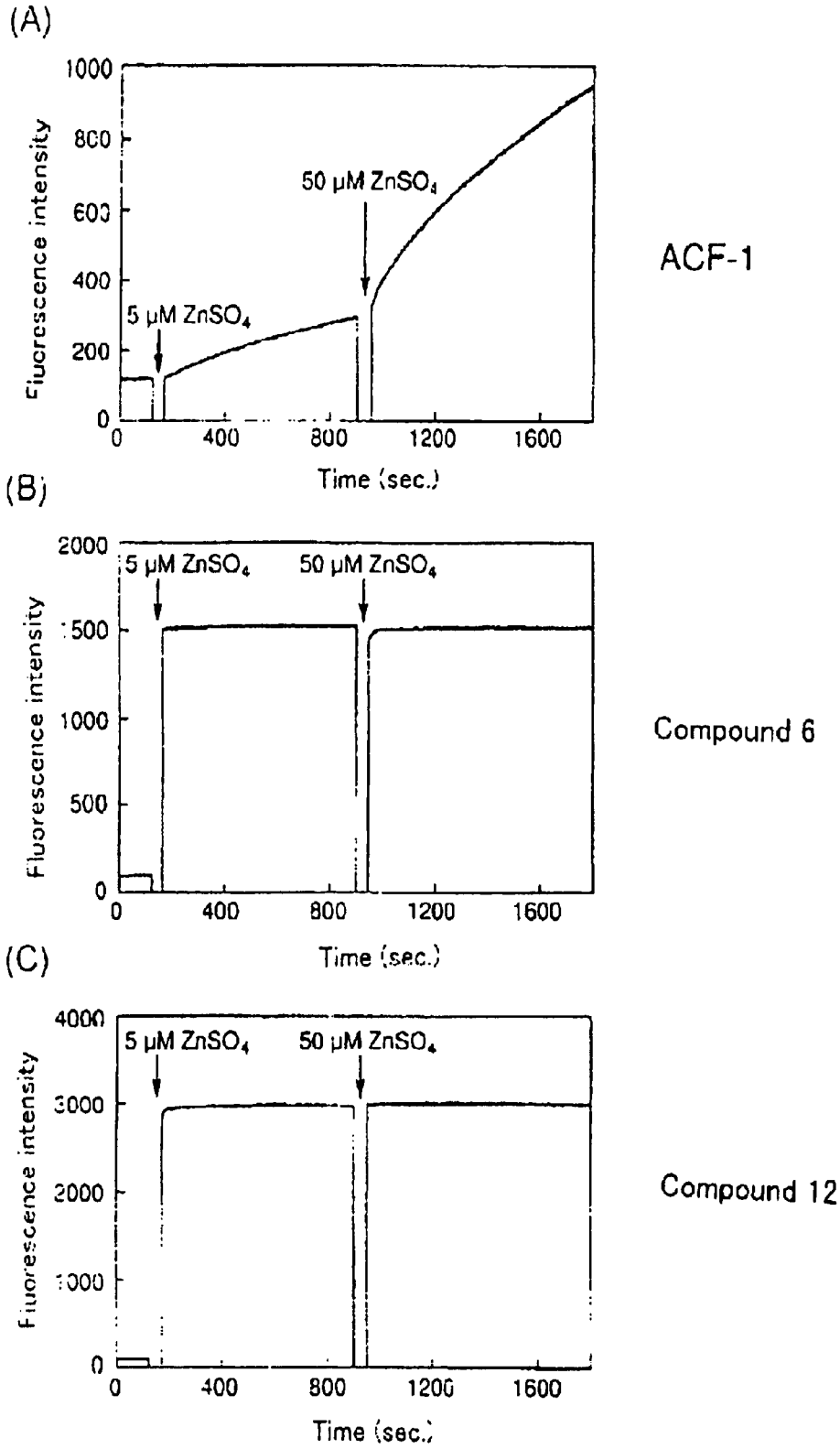
FIG. 4 shows results of a comparison of changes with time in fluorescence intensity between the fluorescent probes for zinc according to the present invention (Compound 6 and Compound 12) and ACF-1 having a cyclic polyamine moiety.

Zinc ion (final concentration 5 μM or 50 μM) was added in 100 mM HEPES (pH 7.5) containing 5 μM Compound 6, Compound 12, or ACF-1 (a compound having a cyclic polyamine moiety described as Compound (20) in Example 1 in Japanese Patent Applications No.(Hei) 11-40325) to measure fluorescence intensity. The fluorescence intensity was measured at the excitation wavelength of 491 nm and the fluorescence wavelength of 513 nm for Compound 6, the excitation wavelength of 492 nm and the fluorescence wavelength of 514 nm for Compound 12, and the excitation wavelength of 495 nm and the fluorescence wavelength of 515 nm for ACF-1. The results are shown in FIG. 4. In the figure, the ordinate axis represents relative fluorescence intensity. As clearly indicated the results, the fluorescence intensity is not instantly increased by ACF-1, whilst fluorescence intensities were instantly increased by Compound 6 and Compound 12 of the present invention. Accordingly, the use of the compound according to the present invention enables very quick detection of zinc, and also enables the detection of rapid change in the concentration of zinc.

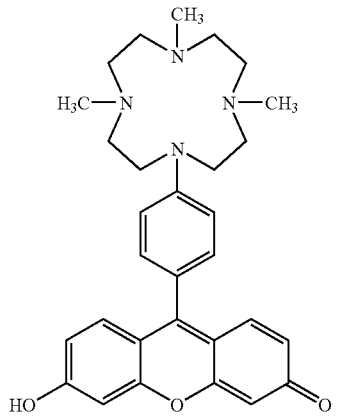

ACF-1

Example 6

Figure 5:
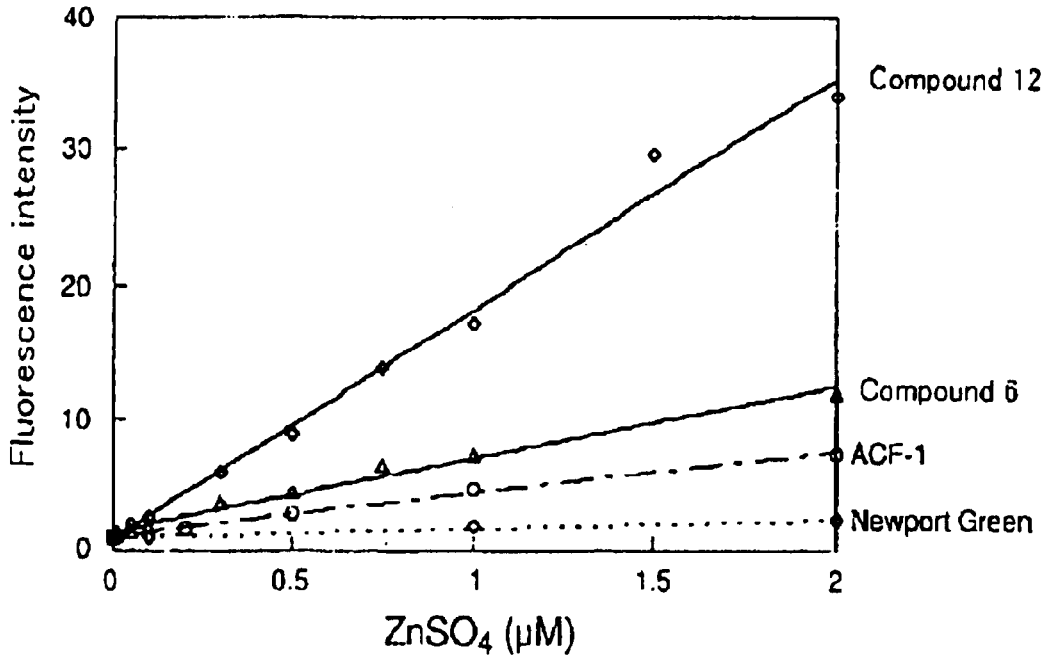
FIG. 5 shows a correlation between fluorescence intensity of the fluorescent probes for zinc according to the present invention (Compound 6 and Compound 12) and zinc ion concentration.

Zinc ions at various concentrations were added in 100 mM HEPES buffer (pH 7.5) containing 5 μM Compound 6, Compound 12, ACF-1, or Newport Green (Handbook of Fluorescent Probes and Research Chemicals, 6th Edition by Richard P. Haugland, pp. 531–540), and changes in fluorescence intensity were measured. The fluorescence intensity was measured at the excitation wavelength of 491 nm and the fluorescence wavelength of 513 nm for Compound 6, the excitation wavelength of 492 nm and the fluorescence wavelength of 514 nm for Compound 12, the excitation wavelength of 495 nm and the fluorescence wavelength of 515 nm for ACF-1, and the excitation wavelength of 505 nm and the fluorescence wavelength of 530 nm for Newport Green. The results are shown in FIG. 5. In the figure, the fluorescence intensities on the ordinate axis are shown as numerical values with addition of each metal ion relative to the fluorescence intensity without addition of metal ion which is taken as 1. Compound 6 and Compound 12 of the present invention exhibited a high detection sensitivity. In particular, the detection sensitivity of Compound 12 was very high, which verifies an optimum combination of the chelater moiety and the fluorescence-emitting moiety of the compound.

Example 7

Figure 6:
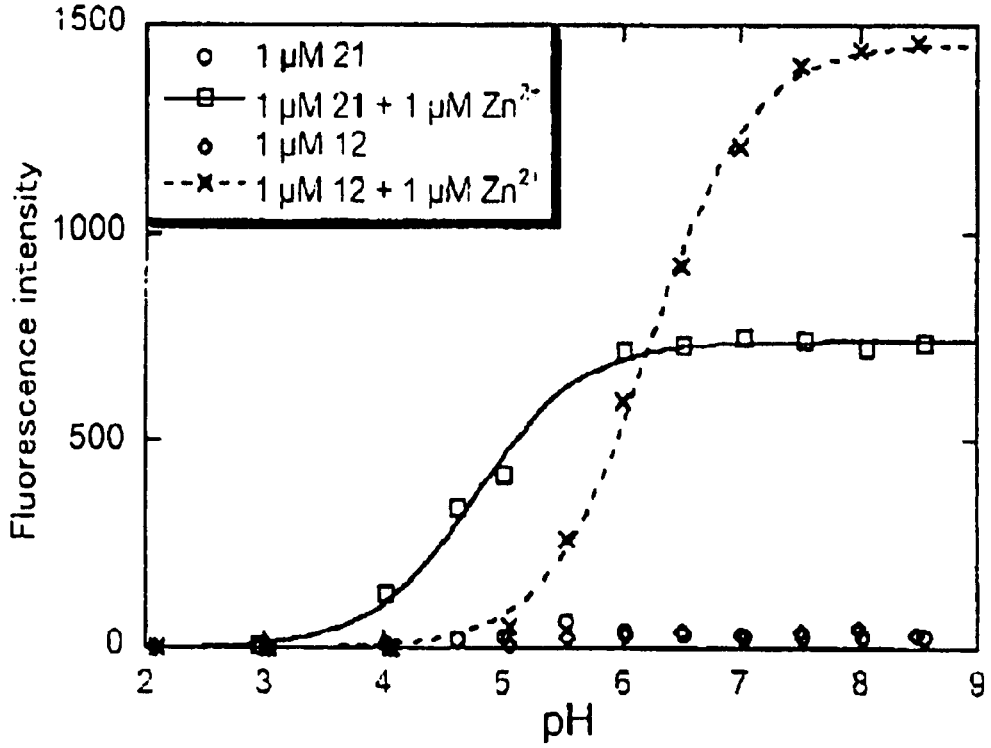
FIG. 6 shows changes in fluorescence intensity of Compound 12, Compound 21, and zinc complexes thereof with relation to pH changes.

Changes in fluorescence intensity of Compound 12, Compound 21, and zinc complexes thereof were investigated with relation of pH changes. The fluorescence intensity was measured at the excitation wavelength of 492 nm and the fluorescence wavelength of 514 nm for Compound 12, and the excitation wavelength of 505 nm and the fluorescence wavelength of 522 nm for Compound 21. The results are shown in FIG. 6.

Buffers used are as follows.

100 mM $Cl_2CHCOOH$—$Cl_2CHCOONa$ buffer (pH 2.0)

100 mM $ClCH_2COOH$—$ClCH_2COONa$ buffer (pH 3.0)

100 mM AcOH-AcONa buffer (pH 4.0, 4.5, 5.0)

100 mM MES buffer (pH 5.5, 6.0, 6.5)

100 mM HEPES buffer (pH 7.0, 7.5, 8.0)

100 mM CHES buffer (pH 8.5)

The fluorescence intensity of Compound 21 was more stable than Compound 12 at pH of around 7.4 which is an intercellular pH, which indicates that the probe is hardly influenced by intercellular pH changes.

Example 8

The change in fluorescence intentiy by ischemic stimulus was investigated using a rat hippocampal slice.

Figure 7:
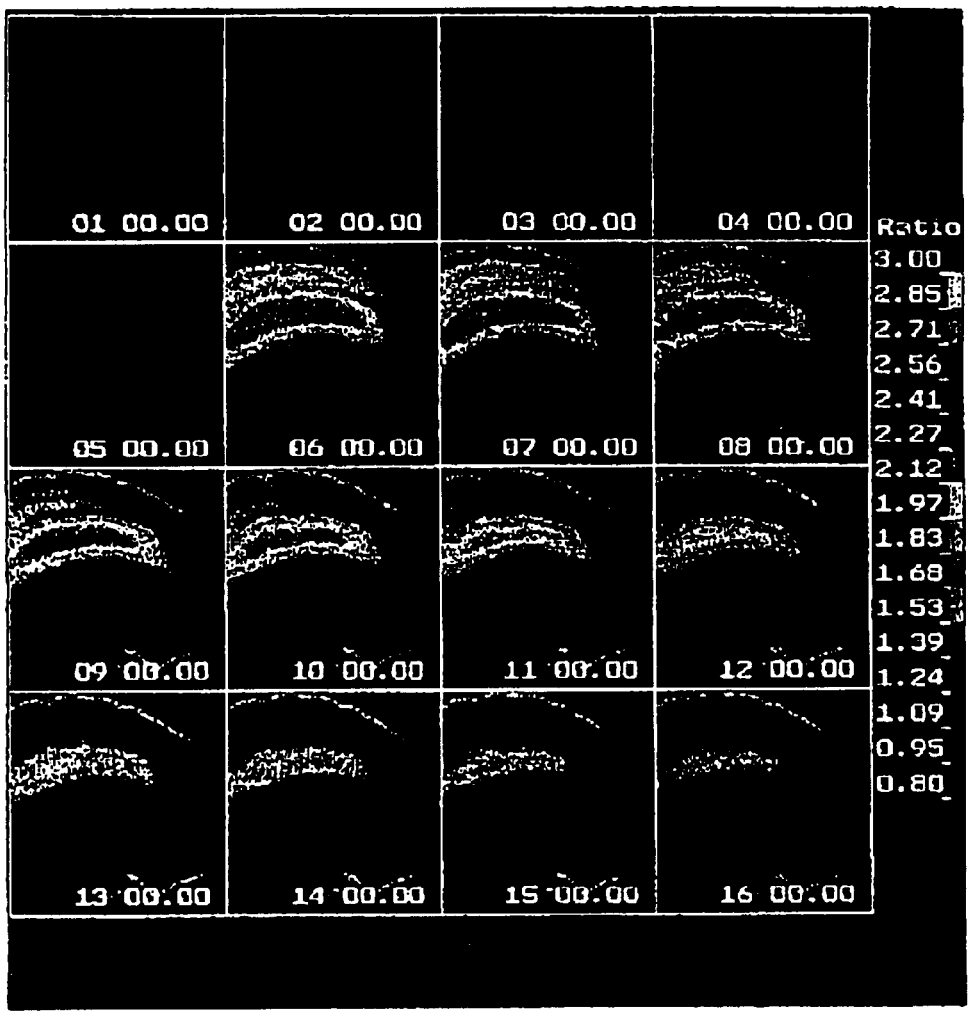
FIG. 7 shows a result of investigation on changes in fluorescence intensity by ischemic stimulus using a rat hippocampal slice.

10 μM of Compound 22 was added to a rat hippocampal slice and incubated, and then the slice was subjected to ischemic stimulus for 10 minutes (2 to 12 minutes in the drawing) to observe a change with time in fluorescent images. The results are shown in FIG. 7.

For preparation of the hippocampal slice, Ringer's solutions having the following formulations were used.

(1) Ringer's solution

Formulation: 124 mM NaCl, 1.25 mM $NaH_2PO_4$, 2.5 mM KCl, 2 mM $CaCl_2$, 26 mM $NaHCO_3$, 1 mM Mg $Cl_2$, 10 mM glucose (2) Ringer's solution for ischemia Formulation: 124 mM NACl, 1.25 mM $NaH_2PO_4$, 2.5 mM KCl, 2 mM $CaCl_2$, 26 mM $NaHCO_3$, 1 mM $MgCl_2$, 10 mM 2-deoxyglucose (3) Chlorine-Ringer's solution Formulation: 124 mM choline, 1.25 mM $NaH_2PO_4$, 2.5 mM KCl, 0.5 mM $CaCl_2$, 26 mM $NaHCO_3$, 2.5 mM $MgCl_2$, 10 mM glucose The Ringer's solutions used for the preparation and measurement of the slices were kept under constant bubbling of 95% $O_2$/5% $CO_2$.

A Wistar rat (200 to 250 g, male) was anesthetized with ether. After decapitation, the whole brain was rapidly extirpated and put into the ice-cooled chorline-Ringer's solution, and allowed to stand for 10 minutes. After the brain was cut into left and right hemispheriums or Shale loaded with the ice-cooled choline-Ringer's solution and the sorbet-like choline-Ringer's solution, the interbrain was removed and the hippocampus was taken out using a spatula. The hippocampus was placed on agar and fixed to the agar with pins, and sliced in the width of 300 μm using a rotary slicer. The sliced hippocampus was put into the Ringer's solution heated to 30° C. and allowed to stand for 30 minutes to 1 hour. The sliced hippocampus was kept in the Ringer's solution at room temperature until it was put to use.

Subsequently, a 10 mM solution of Compound 22 dissolved in DMSO was diluted to 10 μM with the Ringer's solution. The sliced hippocampus was put into the resulting solution and incubated under a shaded condition at room temperature for 1.5 hour. After the sliced hippocampus was put into the fresh Ringer's solution and washed for about 30 minutes to 1 hour and 30 minutes, and then transferred into a chamber and subjected to measurement. The warmed Ringer's solution was circulated (flow rate of 2 to 3 ml/minute) in the chamber to constantly keep the temperature at 33 to 34° C. Measurement was carried out using an inverted microscope (Olympus IX-70, objective lens: 4x, dichroic mirror: 505 nm).

Ischemic stimulus was carried out by exchanging the Ringer's solution circulated in the chamber in the following manner.

Ringer's solution (95% $O_2$+5% $CO_2$ bubbling): 2 minutes (01 00.00 to 02 00. 00 in the figure)→Ringer's solution for ischemia (95% $N_2$+5% $CO_2$ bubbling): 10 minutes (03 00. 00 to 12 00. 00 in the figure)→Ringer's solution (95% $O_2$+5% $CO_2$ bubbling): 4 minutes (13 00. 00 to 16 00. 00 in the figure).

As a result, in the CA1 region, where cell death was reported to be caused by ischemic stimulus, the fluorescence intensity was found to be increased about 3 minutes after the initiation of ischemic stimulus.

Figure 8:
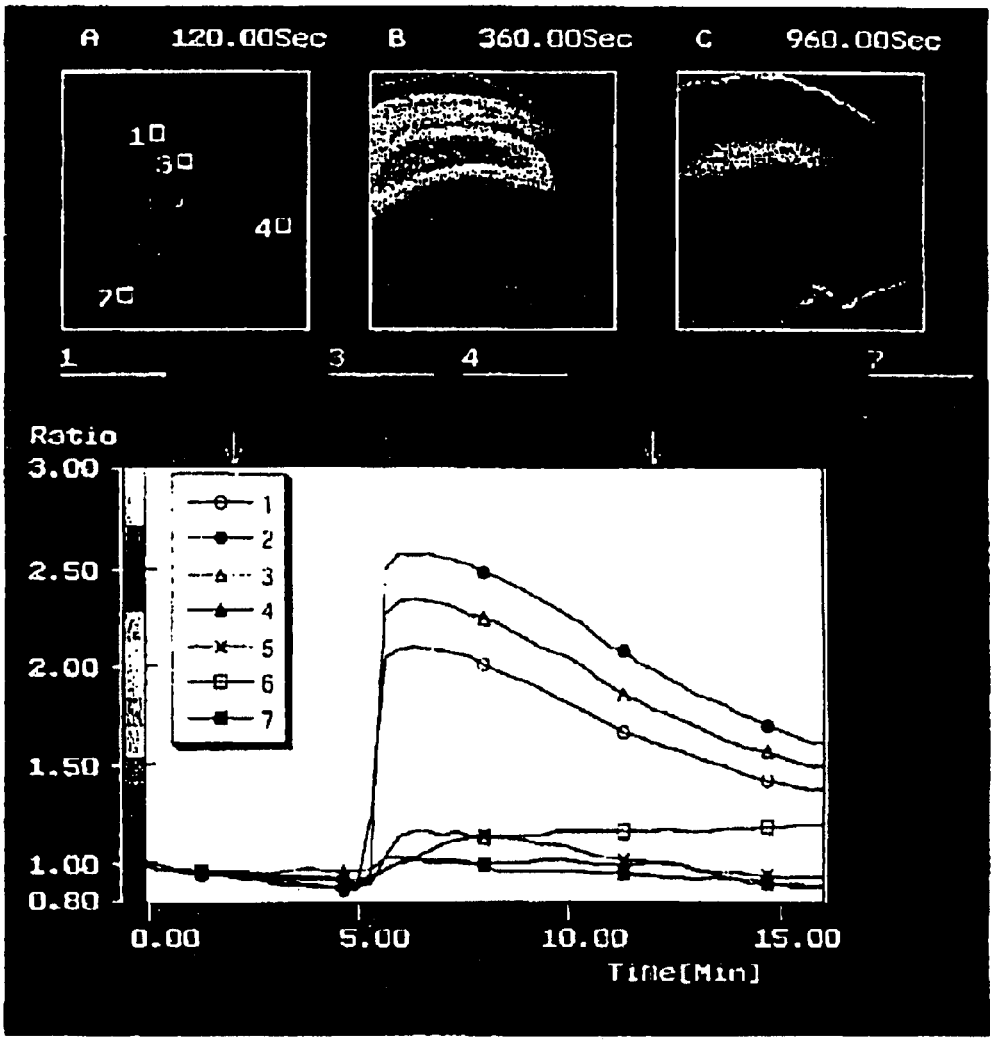
FIG. 8 shows a result of investigation on changes in fluorescence intensity in each of regions by ischemic stimulus using a rat hippocampal slice.

Further, the fluorescence intensity was most remarkably increased in the CA1 region (1, 2, 3 in the drawing) after ischemic stimulus as shown in FIG. 8. The fluorescence intensity was also increased in the CA3 region (site 4 in the figure) and the dentate gyrus (sites 6 and 7 in the figure). The ordinate axis of the graphs shows fluorescence intensity at the time of initiation of measurement (0.00 sec) which is taken as 1.00.

INDUSTRIAL APPLICABILITY

The compound of the present invention is useful as a fluorescent probe for measurement of zinc. More specifically, the compound of the present invention is characterized to form a complex with zinc very quickly and detection sensitivity is very high. Accordingly, the compound of the present invention is very useful as an agent for accurately measuring rapid changes in concentration of zinc ions in a living organism.

What is claimed is:

1. A compound represented by general formula (IB) or a salt thereof:

(IB)

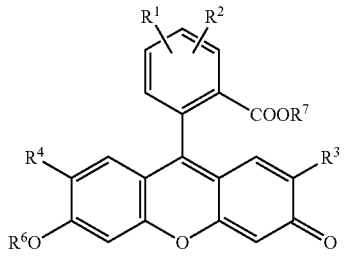

wherein $R^1$ and $R^2$ independently represent a hydrogen atom or a group represented by formula (A):

(A)

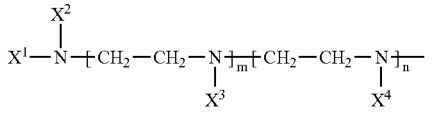

wherein $X^1$, $X^2$, $X^3$, and $X^4$ independently represent a hydrogen atom, an alkyl group, a 2-pyridylmethyl group, or a protective group for an amino group, and m and n independently represent 0 or 1, *and at least one of m and n is 1,* provided that $R^1$ and $R^2$ do not simultaneously represent hydrogen atoms; $R^3$ and $R^4$ independently represent a hydrogen atom or a halogen atom;

$R^6$ represents a hydrogen atom, an alkylcarbonyl group, or an alkylcarbonyloxymethyl group, and $R^7$ represents a hydrogen atom or an alkyl group.

2. A compound represented by general formula (II) or a salt thereof:

(II)

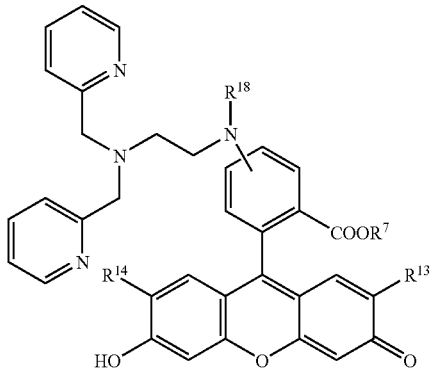

wherein $R^{13}$ and $R^{14}$ independently represent a hydrogen atom or a halogen atom; $R^{17}$ represents a hydrogen atom or an alkyl group; and $R^{18}$ represents a hydrogen atom or a protective group for an amino group.

3. The compound or a salt thereof according to claim 2, wherein $R^{17}$ and $R^{18}$ independently represent hydrogen atoms.

4. The compound or a salt thereof according to claim 2, wherein both of $R^{13}$ and $R^{14}$ are hydrogen atoms, or both of $R^{13}$ and $R^{14}$ are chlorine atoms.

5. A compound represented by general formula (IIIB) or a salt thereof:

(IIIB)

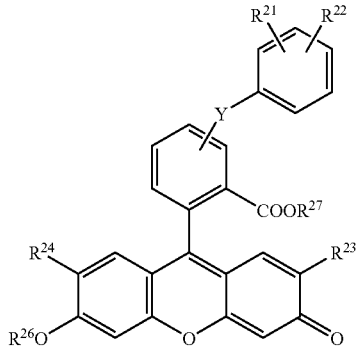

wherein $R^{21}$ and $R^{22}$ independently represent a hydrogen atom or a group represented by formula (B):

(B)

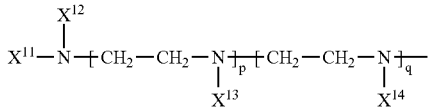

wherein $X^{11}$, $X^{12}$, $X^{13}$, and $X^{14}$ independently represent a hydrogen atom, an alkyl group, a 2-pyridylmethyl group, or a protective group for an amino group, and p and q are independently 0 or 1, provided that $R^{21}$ and $R^{22}$ do not simultaneously represent hydrogen atoms; Y represents —CO—NH— or —NH—CO—; $R^{23}$ and $R^{24}$ independently represent a hydrogen atom or a halogen atom; $R^{26}$ represents a hydrogen atom, an alkylcarbonyl group, or an alkylcarbonyloxymethyl group; and $R^{27}$ represents a hydrogen atom or an alkyl group.

6. A fluorescent probe for zinc which comprises a compound according to claim 1, provided that a compound is excluded wherein a protective group for an amino group is introduced, or a salt thereof.

7. A zinc complex which is formed by a compound according to claim 1, provided that a compound is excluded wherein a protective group for an amino group is introduced, or a salt thereof together with a zinc ion.

8. A method for measuring a zinc ion which comprises (a) reacting a compound according to claim 1, provided that a compound is excluded wherein a protective group for an amino group is introduced, or a salt thereof with a zinc ion to form a zinc complex; and measuring fluorescence intensity of the zinc complex.

9. The compound or a salt thereof according to claim 3, wherein both of $R^{13}$ and $R^{14}$ are hydrogen atoms, or both of $R^{13}$ and $R^{14}$ are chlorine atoms.

* * * * *

UNITED STATES PATENT AND TRADEMARK OFFICE

CERTIFICATE OF CORRECTION

PATENT NO. : RE 40,572 E
APPLICATION NO. : 11/808125
DATED : November 11, 2008
INVENTOR(S) : Nagano et al.

It is certified that error appears in the above-identified patent and that said Letters Patent is hereby corrected as shown below:

On the cover page (64) Related U.S. Patent Documents, of the printed patent, "Jul. 7, 2005" should be --June 7, 2005--.

Signed and Sealed this

Thirty-first Day of March, 2009

John Doll

JOHN DOLL
*Acting Director of the United States Patent and Trademark Office*